United States Patent [19]

Prota et al.

[11] Patent Number: 5,603,734
[45] Date of Patent: Feb. 18, 1997

[54] HAIR DYEING WITH PERSULFATE OXIDANTS AND CATECHOLS

[75] Inventors: Guiseppe Prota, Naples, Italy; Gottfried Wenke, Woodbridge, Conn.

[73] Assignee: Clairol Incorporated, Stamford, Conn.

[21] Appl. No.: 484,191

[22] Filed: Jun. 7, 1995

Related U.S. Application Data

[63] Continuation of Ser. No. 174,490, Dec. 27, 1993, abandoned.

[51] Int. Cl.⁶ .................................................. A61K 7/13
[52] U.S. Cl. .................... 8/424; 8/406; 8/407; 8/408; 8/623; 8/624
[58] Field of Search ............................. 8/405, 406, 407, 8/408, 424, 435, 623, 624

[56] References Cited

U.S. PATENT DOCUMENTS

| | | | |
|---|---|---|---|
| 3,658,454 | 4/1972 | Paul | 8/10 |
| 3,993,436 | 11/1976 | Fujinuma | 8/10.2 |
| 4,021,538 | 5/1977 | Yu et al. | 8/10.1 |
| 4,390,341 | 6/1983 | Jacobs | 8/405 |
| 4,453,941 | 6/1984 | Jacobs | 8/405 |
| 4,746,322 | 5/1988 | Herlihy | 8/405 |
| 4,776,857 | 10/1988 | Carroll et al. | 8/423 |
| 4,904,274 | 2/1990 | Schultz et al. | 8/406 |
| 5,273,550 | 12/1993 | Prota et al. | 8/405 |
| 5,279,617 | 1/1994 | Prota et al. | 8/406 |
| 5,279,618 | 1/1994 | Prota et al. | 8/406 |

*Primary Examiner*—Paul Lieberman
*Assistant Examiner*—Caroline L. Dvsheck
*Attorney, Agent, or Firm*—Charles J. Zeller

[57] ABSTRACT

A process of dyeing hair by preparing and applying to the hair an aqueous reaction medium buffered to a pH of from 7 to 11 with a bicarbonate or a TRIS buffer, a catalytic quantity of a cupric or ferrous salt, a catechol and a persulfate oxidizing agent and removing the composition after the desired color is attained, and compositions and kits for practicing such process. The composition may be formed by simultaneous addition of the catechol and the oxidant to the hair or by addition of the catechol followed by addition of the oxidant.

22 Claims, No Drawings

HAIR DYEING WITH PERSULFATE OXIDANTS AND CATECHOLS

This application is a continuation of U.S. Ser. No. 08/174,490 filed Dec. 27, 1993, now abandoned.

FIELD OF THE INVENTION

This invention relates to compositions, methods and kits for dyeing hair. More specifically, the invention relates to methods of dyeing hair in which mixtures of certain ortho dihydroxy benzenes, sometimes referred to herein as catechols and substituted catechols or catechol derivatives are oxidized by persulfate oxidation in aqueous media under controlled conditions to produce pigments for permanently coloring human hair. The invention relates also to compositions for conducting the hair dyeing process and to the packaged reactants sold in the form of kits.

The preferred ortho catechols of the invention are 3,4-dihydroxyphenylalanine (dopa) and its derivatives and analogs to treat human hair thereby to impart desirable tints and tones.

BACKGROUND OF THE INVENTION

Certain selected catechols have been previously employed in hair coloring but only in association with primary intermediates. Typically, they give rise to pale yellow to beige colors. In this type of application, the catechols are not oxidized, rather they react with the oxidized form of primary intermediates to form colored pigments.

Catechols have also been oxidized to produce hair colorants with hydrogen peroxide in the presence of peroxidase. See Japan Kokais 78: 32,132; 59:161,308; and 61:56,119. See also Japanese Patent J83031-225B.

French Patent 1,164,951 relates to the use of persulfates or any of a variety of other oxidants to color hair. There is no recognition in the patent of the importance of pH control in the system. The patent states that the hair coloring reaction may take place over a wide pH range and may, in fact, take place at whatever pH results from mixing the principal ingredients. The pH is permitted to vary appreciably during the course of hair coloring as is shown in several of the examples.

Dopa and dopamine are disclosed as oxidative hair dyeing precursors in the process of Herlihy, U.S. Pat. No. 4,746,322, wherein the aqueous hair dyeing composition comprises said precursor, an organic compound to assist dye dispersion and an iodate or periodate. The dopa or dopamine dye precursor is present in the aqueous hair dye composition in an amount of from about 1 to about 100 mg/ml, preferably from about 5 to about 25 mg/ml. Dopamine is preferred, according to Herlihy. The iodate or periodate is present in the composition at a concentration of 1 to about 50 mg/ml, while the dispersing agent is present in an amount of from about 0.1 to 30% (wt./vol.). Optionally, a color modifier can be incorporated into the aqueous composition of Herlihy, at a level of from about 0.1 to about 10 mg/ml. pH may be maintained between about 3 to 7 by incorporation of an effective amount of a buffer. According to the patent, the above described aqueous compositions disperse the dye on the hair shaft "with little or no penetration into the hair shaft", Column 2, lines 56–58.

Int. Appl. WO 93/05,759, owned by the assignee of this patent application describes a melanin-forming hair dye, characterized by the in situ formation of dihydroxy indole (DHI) from dopa. Ferricyanide or permanganate are used to oxidize dopa to DHI. There is no teaching or suggestion of persulfate oxidation.

Ammonium persulfate which is the presently preferred persulfate for use in this invention is a well known oxidizing agent as are the corresponding alkali and alkaline earth metal persulfates. All are useful in this invention.

BRIEF SUMMARY OF THE INVENTION

It has now been discovered that desirable colors can be achieved in human hair by contacting the hair with an oxidizing composition buffered to a pH of from about 7 to 11 with a bicarbonate or TRIS buffer in the presence of a catalytic quantity of a water soluble copper or ferrous salt together with a tinctorially effective amount of at least one catechol and a persulfate oxidizing agent and allowing the composition to remain in contact with the hair to achieve a desired color.

Among the important advantages achieved by the practice of this invention, one of the most significant is that the oxidation is accomplished without the use of hydrogen peroxide, thereby avoiding the known disadvantages of this oxidizing agent. Another is that the presently preferred oxidative substrates include dopa and its analogs and derivatives which are known intermediates in human melanogenesis. These substrates are expected, therefore, to be toxicologically acceptable and to produce natural tones. Still another advantage is that at least some of the end products of the oxidation reaction are expected to be closely related to trichochromes or phaeomelanins the natural red and yellow pigments depending on the particular catechol derivative used. Thus, by the practice of this invention it is possible to achieve natural appearing red and yellow hair tones which have heretofore eluded the art.

A careful selection of the oxidation conditions, in particular the choice of buffer and catalyst, allows the conversion of catechols to o-quinones in yields that are high enough to impart a desired permanent color to hair. The presently preferred buffer is TRIS. The presently preferred catalyst is copper-II.

If dopa is used as the catechol, the process of the invention is capable of producing melanin-like pigments (through formation and oxidative polymerization of DHI). On the other hand, a range of colors can be obtained if dopaquinone, an intermediate in the formation of DHI, is trapped with color modifiers. Suitable modifiers include, for example, couplers, primary intermediates and direct dyes.

Cysteinyldopas can be used as the catechol in the invention to form phaeomelanin-like pigments.

DETAILED DESCRIPTION OF THE INVENTION

The hair dyeing process of the present invention comprises the preparation of an aqueous hair dyeing composition comprising a catechol, optionally a color modifier, and a persulfate oxidant and contacting it with hair to be treated in an aqueous medium under carefully controlled conditions for a period of time which is less than one hour. When dopa or derivatives of dopa are used as the catechol, the reaction can proceed in such manner and under such conditions as to provide an amount of a melanin-forming hair dye precursor during the period of contact effective to generate an amount of melanin in the hair which is effective to impart a permanent color. The precursor(s) diffuses into the hair during the period of contact and forms pigments in situ in the hair to provide the desired permanent color.

Preferably, the contact time of the hair dyeing composition on the hair is from about 5 to 45 minutes, most preferably from about 5 to about 30 minutes.

By "permanent" is meant a color not removable by shampooing with a conventional surfactant-containing shampoo, the permanency being attributable to the inability of the pigment to diffuse from the hair shaft in view of its molecular size.

By "melanin" is meant a synthetically derived pigment having a dark color formed by polymerization of a melanin precursor.

By "melanin-forming precursor" is meant the reaction product(s) of the selected catechol of the present invention, which reaction product(s) undergoes polymerization to form melanin. Such melanin precursors generically are nitrogenous phenolic compounds and may be indolic compounds, except to the extent that cyclization to form the indole ring might be prevented in view of reactions occurring with direct hair dyes, hair dye couplers and/or primary intermediates, as hereinafter explained.

Inasmuch as the general reaction scheme leading to the formation of melanin have been studied by various investigators, applicants believe that the terms "melanin" and "melanin precursor" as used herein with respect to the reaction products of the selected catechol of this invention are terms which are well understood by one of ordinary skill in the field, even though the chemical identity of the melanin precursors, particularly those precursors formed by reaction with direct dyes, primary intermediates and/or couplers in accordance with the process of the present invention, is not precisely known or understood.

By "applying" is meant contacting the hair to be dyed with a composition of the invention which is formed on the hair or just prior to contact with the hair, in a sufficient amount to effect a color change of the hair.

The amount of substituted oxidative substrate which will be tinctorially effective depends upon many factors which can be readily evaluated by the skilled artisan either from experience or from a few simple tests. These factors include, for example, the color desired, the selected coloring agent or agents, the original color of the hair to be treated, the pH, auxiliary coloring agents employed, etc. Typically, however, the compositions of the invention will contain from about 0.1 to 10% by weight colorant i.e. catechol, preferably 0.1 to 2%.

All percents by weight defined in this specification and claims are percents by weight based on the total weight of the composition.

The "contact time" as that term is employed herein is the period of time from the mixing of the reactants to the removal from the hair.

The Catechol Species

A wide variety of catechols can be utilized in the practice of this invention. The presently preferred catechols are dopa species. The term "dopa species" includes dopa itself as well as homologs, analogs and derivatives of DOPA. It includes, for example cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

Typically useful catechols in addition to the dopa species include those represented by the formula:

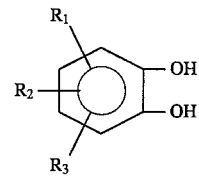

wherein $R_1$, $R_2$ and $R_3$, which may be the same or different, are electron donor or acceptor substituents selected from the group consisting of H, $C_1$–$C_6$ alkyl, OH, OR, COOR, NHCOR, CN, COOH, Hal, $NO_2$, $CF_3$, $SO_3H$ and $NR_4R_5$, with the proviso that only one of $R_1$, $R_2$ or $R_3$ is CN, COOH, Hal, $NO_2$, $CF_3$, or $SO_3H$; $R_4$ and $R_5$, which may be the same or different, are H, $C_1$–$C_6$ alkyl or substituted $C_1$–$C_6$ alkyl in which the substituent may be OH, OR, $NHCOR_6$, $NHSO_2R_6$, $NHCONH_2$, $NHCO_2R_6$, $NHCSNH_2$, CN, COOH, $SO_3H$, $SO_2NR_6$, $SO_2R_6$, or $COOR_6$; $R_6$ is $C_1$–$C_6$ alkyl, $C_1$–$C_6$ hydroxyalkyl, phenyl linked to the nitrogen by an alkylene chain, phenyl or substituted phenyl with substituents defined as $R_1$, and R is $C_1$–$C_6$ alkyl or $C_1$–$C_6$ hydroxyalkyl.

It will be understood and apparent to the skilled artisan that this general formula does not represent all of the ortho catechols which will serve as oxidizable substrates in accordance with the practice of this invention.

The Oxidant Component

The oxidant employed in this invention is a water soluble persulfate salt. More specifically, it is ammonium persulfate or an alkali metal persulfate, preferably sodium or potassium persulfate. Of these, sodium persulfate is most preferred because the potassium salt is less soluble and tends to form unwanted precipitates. The concentration of the oxidant can vary from about one equivalent to about four equivalents, with respect to the catechol substrate(s). The oxidation conditions should be such that diffusion of precursors into the hair can compete with the rate of formation of pigments, which are too large to diffuse into the hair. This means, for example, that when oxidation catalyst is used as provided in this invention, the concentration of oxidant should not greatly exceed two equivalents so as to keep the oxidation of catechols at moderate rates.

The Buffering Agent Component

Surprisingly, it has been found, that the rate of oxidation of catechols with persulfate depends strongly on the buffer, which is used to control the pH of the reaction medium. To demonstrate this, dopa (1 mM) was oxidized in aqueous buffers at various pH values with ammonium or sodium persulfate. The rate of oxidation of dopa was monitored by measuring spectrophotometrically, at 475 nm, the amount of dopachrome which formed, this compound being a known intermediate in the formation of melanin from dopa. Scattering effects due to the formation of melanin were estimated from the absorbency at 700 nm and properly subtracted. At pH 6.8, for example, the yield of dopachrome from dopa (1 mM) with 4 mM persulfate is:

1% in 0.1M phosphate, HEPES and citrate buffers
3% in 0.1M acetate
4% in 0,1M sodium bicarbonate
6% in 0.1M TRIS buffer Thus, TRIS buffer and sodium bicarbonate are preferred buffers for use in combination with persulfates. The effect of buffers in hair dyeing with persulfates and catechols is demonstrated in Examples 1–4.

Oxidation Catalyst

It is well known, that persulfate oxidation can be catalyzed by transition metal cations. Surprisingly, it was found that cupric and ferrous ions are far more effective than other ions known for this purpose and therefore more useful during oxidation of catechols for the purpose of dyeing hair. For example, the oxidation of dopa (1 mM, bicarbonate buffer, pH 8.5) was accelerated two-fold by ferrous ions (0.1 mM) and more than 5-fold by cupric ions (0.1 mM).

The maximum catalytic effect of copper ions on the conversion of dopa to dopachrome is observed in TRIS buffer. It is believed that TRIS more efficiently binds the metal thereby enhancing its oxidizing capacity. Any of a variety of water soluble ferrous or cupric salts may be employed. Cupric acetate, sulfate and chloride are preferred.

Advantages of the Invention

Contrary to the teachings of the prior art, it has been discovered that control of pH during the complete coloring process is an important parameter in the production of hair coloring pigments utilizing ortho catechols. Moreover, it has been found that the selection of specific buffers and oxidation catalysts are important control elements.

When operating within the defined parameters of this invention it is possible to control the rate of formation of useful pigments so that they are formed within the hair strand in high concentration to provide intense color formation.

There are a number of variations in the procedure of this invention which can be employed to achieve the desired results. These include, for example, the one and the two step processes.

In the one step or simultaneous procedure, the mixture of hair colorant and oxidizing agent in aqueous medium under the selected conditions maintained in contact with the hair until sufficient oxidation products are formed to effect the desired result. The hair is then rinsed and dried.

In the two step or sequential process, the colorant in an aqueous medium under the selected conditions is applied to the hair and left for a period of from about 1 to 30 minutes preferably 10 to 20 minutes. The aqueous solution of the oxidant is then brought into contact with the hair for another 1 to 20 minutes preferably 2 to 10 minutes until the desired coloration is attained. The hair is then rinsed and dried.

A further aspect of the present invention is the optional incorporation of a hair color modifier selected from the group consisting of one or more direct dyes, primary intermediates, couplers and mixtures thereof in the oxidation mixture. It is believed that these components when present react at least in part with the intermediate compounds formed during pigment production thereby providing additional chromatic characteristics to the pigments ultimately obtained. When such color modifiers are employed, the amount of oxidant in the reaction mixture is increased to provide for the oxidation of these materials since some of them will be directly oxidized in the usual way rather than reacting with an intermediate of the primary reaction sequence. It will be apparent to the skilled artisan that by use of these auxiliary coloring agents, a wide variety tints, tones and shades can be achieved.

The concentration of hair color modifiers is normally less than about 10 mg/ml, and preferably is present in the reaction medium from about 0.01 to about 5 mg/ml, most preferably from about 0.05 to about 2 mg/ml. The amount of these components should not be so great as to prevent the formation of the principal pigment. That is, the process of the present invention contemplates reaction of only a portion of the intermediate reaction products with the hair color modifiers.

A wide variety of direct dyes, primary intermediates and couplers are known to the skilled artisan and can be employed in this invention.

The presently preferred primary intermediates and couplers include:
Primary p-phenylenediamine
Intermediates: p-aminophenol o-aminophenol N,N-bis(2-hydroxyethyl)-p-phenylenediamine 2,5-diaminopyridine p-toluenediamine
Couplers: resorcinol m-aminophenol α-naphthol 5-amino-o-cresp; 2-methylresorcinol N-acetyl dopa 4,6-di(hydroxyethoxy)-m-phenylenediamine m-phenylenediamine Suitable direct dyes include, for example, nitro dyes, azo dyes and anthraquinone dyes.

The variously described embodiments of the present invention may also include in the hair dye composition one or more optional ingredients, which may be provided in one or more additional containers of the kits to be described in more detail hereinafter for admixture by the user into the aqueous reaction mixture, or, if compatible, may be incorporated into the oxidant or colorant premix solutions described previously.

Such ingredients include well-known, conventional additives usually employed in oxidative hair coloring compositions such as organic solvents, thickeners, surface-active agents to assist in penetration of the hair shaft, pH adjusting agents, antioxidants, fragrances.

The hair dye compositions used in the process of the present invention can include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%. Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether. The cosolvent is one that is only minimally oxidized by the oxidant or, preferably, oxidation resistant.

Surface-active agents employed in the dyeing compositions of this invention can be anionic, nonionic, cationic, amphoteric or zwitterionic. By way of examples of the various types of surface-active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylnaphthalene sodium sulfonate; dioctyl sodium sulfonsuccinate; sodium N-methyl-N-oleoyl taurate; oleic acid ester of sodium isethionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

A thickening agent may also be incorporated in the dyeing composition of this invention, which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cps to about 100,000 cps. For a typical lotion formulation, composition viscosity is between about 100 cps to about 10,000 cps, at which viscosity the composition can be applied to the hair without running or dripping.

The list of optional ingredients is not intended as limiting. Other suitable adjuvants for inclusion in the hair dye composition are recited, for example, in Zviak, *The Science of Hair Care* (1986) and Balsam and Sagarin, *Cosmetics: Science and Technology*, Vol. 2 (Second Edition 1972).

The process of the present invention may conveniently be practiced by providing premeasured amount of the reactants in separate containers packages in kit form. The user simply admixes the reactants for application to the hair in accordance with the selected practice of the invention. It will be apparent that no special expertise is required to carry out the process, and accordingly the product and process are equally suitable for in-home use by the nonprofessional as well as salon use by the professional. Advantageously, the product in kit form is shelf-stable and is therefore suitable for retain sale without precautions required for some hair colorant compositions, e.g., storage under anaerobic conditions.

The kit provided in accordance with this aspect of the invention comprises a first container containing the oxidizable colorant and a second container containing the oxidant. The selected buffer may be packaged in a third container, or it may be present in the first or second container. Selected modifiers may be mixed with the basic hair colorant of the invention or may be in separate containers.

While the kit may include packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers containing the optional constituents may be provided in the kit. The optional constituents may also be contained within the solutions of the previously described containers, barring any incompatibility.

The consumer admixes the components of the kit, suitable as the aqueous solutions or as dry powders and water, according to written instructions, to obtain the aqueous reaction mixture. Mixing may be conducted in a separate vessel supplied with or external to the kit, or may take place in a container of the kit adapted to provide sufficient head space for mixing. The reactants may also be admixed on the hair of the user. Reaction commences upon mixing. The hair colorant will subsequently oxidize as described herein whereby a permanent hair color is obtained. After the desired hair shade is reached, most preferably within about 30 minutes, the hair dye composition that was applied to the hair is removed, preferably with a conventional shampoo.

In the examples, the colors are evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greenness. Similarly, positive b values indicate yellowness, while negative b values indicate blueness. The L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Priximate to 0 and proximate to 100 hair color intensity apparent to the human eye varies minimally with unit changes in the L value. Between values of about 20 to about 50, hair color intensity varies significantly with unit changes in L value. Thus, the Hunter values are more sensitive in the region where the human eye is able to perceive color changes.

EXAMPLES

The following examples demonstrate, that the choice of buffer has an important effect on the dyeing results with catechols/persulfate Example 1:

0.8 mmole dopa and 0.2 mmole m-aminophenol were dissolved in 10 ml phosphate buffer (7 mmole $Na_2HPO_4$ in 10 ml aqueous HCl; pH 7.4). 0.8 mmole sodium persulfate were added and dissolved in less than one minute. Gray hair was exposed to this dyeing mixture for 30 minutes, rinsed and dried. Hunter values were:

Before dyeing: L 38.2 a 0.2 b 7.8

After dyeing: L 28.5 a 1.5 b 7.0

Example 2:

Dyeing conditions were exactly as in example 1, with the only difference, that TRIS buffer was used instead of phosphate buffer (7 mmole TRIS in 10 ml aqueous HCl; pH 7.4). Hunter values were:

Before dyeing: L 38.2 a 0.2 b 7.8

After dyeing : L 24.4 a 1.7 b 6.1

The color of the swatch was darker and more intense than the swatch of example 1.

The following examples demonstrate the effect of buffer (examples 3 and 4) and catalyst (example 5) on dyeing with catechol/persulfate at short dyeing times.

Example 3:

0.8 mmole 4-methylcatechol and 0.4 mmole resorcinol were dissolved in 10 ml phosphate buffer (7 mmole $Na_2HPO_4$ in 10 ml aqueous HCl; pH 7.4). 0.8 mmole sodium persulfate were added and dissolved within less than a minute. Gray hair was exposed to this dyeing mixture for 5 minutes, rinsed and dried. Hunter values were:

Before dyeing: L 35.2 a 0.2 b 7.6

After-dyeing : L 31.9 a 0.8 b 7.5

Example 4:

Dyeing conditions were exactly as in example 3, with the only difference, that TRIS buffer was used instead of phosphate buffer (7 mmole TRIS in 10 ml aqueous HCl; pH 7.4.). Hunter values were:

Before dyeing: L 35.2 a 0.2 b 7.6

After dyeing : L 30.4 a 1.8 b 7.9

The swatch was noticeably redder than the swatch of example 3.

Example 5:

Dyeing conditions were exactly as in example 4, with the only difference, that 0.025 mmole copper-II-acetate were added to the solution before the addition of sodium persulfate.

Hunter values were:

Before dyeing: L 35.2 a 0.2 b 7.6

After dyeing : L 30.0 a 5.3 b 11.7

The swatch was dyed orange-red. The color was significantly more intense than the color of the swatches of either example 4 or example 3.

What is claimed is:

1. A method of permanently coloring hair comprising (a) applying to the hair a hair dye composition comprising a tinctorially effective amount of at least one catechol; a persulfate oxidizing agent present in the composition in an amount equal to about one to four equivalents relative to the catechol, and sufficient buffering agent to provide a composition having a pH of from about 7 to 11, the buffering agent being selected from the group consisting of 2-amino-2-hydroxymethyl-1,3-propanediol and bicarbonate, and (b) allowing the composition to remain in contact with the hair for a period of time sufficient to achieve a desired color, wherein the period of time from the formation of said hair dye composition to the removal of said hair dye composition from the hair is between about 5 to 45 minutes.

2. The method of claim 1 wherein the hair dye composition further comprises a catalytically effective quantity of a water soluble cupric or ferrous salt, whereby the development of color is accelerated.

3. The method of claim 1 or 2 wherein the catechol is selected from the group consisting of dopa, cysteinyl dopa, alpha alkyl dopa having 1 to 4 carbons in the alkyl group, epinephrine, dopa alkyl esters having 1 to 6 carbons in the alkyl group, and compounds represented by the formula

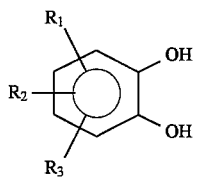

wherein $R_1$, $R_2$ and $R_3$, which may be the same or different, are electron donor or acceptor substituents selected from the group consisting of H, $C_1$–$C_6$ alkyl, OH, OR, COOR, NHCOR, CN, COOH, Hal, $NO_2$, $CF_3$, $SO_3H$ and $NR_4R_5$, with the proviso that only one of $R_1$, $R_2$ or $R_3$ is CN, COOH, Hal, $NO_2$, $CF_3$ or $SO_3H$; $R_4$ and $R_5$, which may be the same or different, are H, $C_1$–$C_6$ alkyl or substituted $C_1$–$C_6$ alkyl in which the substituent may be OH, OR, $NHCOR_6$, $NHSO_2R_6$, $NHCONH_2$, $NHCO_2R_6$, $NHCSNH_2$, CN, COOH, $SO_3H$, $SO_2NR_6$, $SO_2R_6$ or $COOR_6$; $R_6$ is $C_1$–$C_6$ alkyl, $C_1$–$C_6$ hydroxyalkyl, phenyl linked to the nitrogen by an alkylene chain, phenyl or substituted phenyl with substituents defined as $R_1$, and R is $C_1$–$C_6$ alkyl or $C_1$–$C_6$ hydroxyalkyl.

4. The method of claim 3 wherein the catechol is present in the hair dye composition in an amount of from about 0.1 to about 10% by weight.

5. The method of claim 4 wherein the catechol is a dopa species selected from the group consisting of dopa, epinephrine, cysteinyl dopa, alpha alkyl dopa having 1 to 4 carbons in the alkyl group and alkyl dopa esters having 1 to 6 carbons in the alkyl group.

6. The method of claim 5 wherein the dopa species is present in the hair dye composition in an amount of from 0.1 to 2% by weight.

7. The method of claim 6 wherein the dopa species is dopa.

8. The method of claim 4 wherein the hair dye composition is formed on the hair by sequential application to the hair of a catechol-containing aqueous solution and a persulfate-containing aqueous solution.

9. The method of claim 6 wherein the hair dye composition is formed on the hair by sequential application to the hair of a catechol-containing aqueous solution and a persulfate-containing aqueous solution.

10. The method of claim 9 wherein the dopa species is dopa.

11. The method of claim 4 wherein the hair dye composition is formed on the hair by the simultaneous application to the hair of a catechol-containing aqueous solution and a persulfate-containing aqueous solution.

12. The method of claim 6 wherein the hair dye composition is formed on the hair by the simultaneous application to the hair of a catechol-containing aqueous solution and a persulfate-containing aqueous solution.

13. The method of claim 12 wherein the dopa species is dopa.

14. The method of claim 2 wherein the amount of persulfate present in the composition is not in great excess of two equivalents relative to the catechol.

15. The method of claim 2 or 14 wherein the salt is cupric acetate, chloride or sulfate.

16. A hair dyeing kit for permanently dyeing hair which includes in a single package a plurality of containers, the kit comprising (a) a first container containing a tinctorially effective amount of at least one catechol selected from the group consisting of dopa, cysteinyl dopa, alpha alkyl dopa having 1 to 4 carbons in the alkyl group, epinephrine, dopa alkyl esters having 1 to 6 carbons in the alkyl group, and compounds represented by the formula

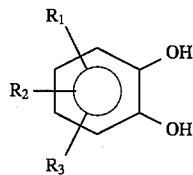

wherein $R_1$, $R_2$ and $R_3$, which may be the same or different, are electron donor or acceptor substituents selected from the group consisting of H, $C_1$–$C_6$ alkyl, OH, OR COOR, NHCOR, CN, COOH, Hal, $NO_2$, $CF_3$, $SO_3H$ and $NR_4R_5$, with the proviso that only one of $R_1$, $R_2$ or $R_3$ is CN, COOH, Hal, $NO_2$, $CF_3$ or $SO_3$; $R_4$ and $R_5$, which may be the same or different, are H, $C_1$–$C_6$ alkyl or substituted $C_1$–$C_6$ alkyl in which the substituent may be OH, OR, $NHCOR_6$, $NHSO_2R_6$, $NHCONH_2$, $NHCO_2R_6$, $NHCSNH_2$, CN, COOH, $SO_3H$, $SO_2NR_6$, $SO_2R_6$ or $COOR_6$; $R_6$ is $C_1$–$C_6$ alkyl, $C_1$–$C_6$ hydroxyalkyl, phenyl linked to the nitrogen by an alkylene chain, phenyl or substituted phenyl with substituents defined as $R_1$, and R is $C_1$–$C_6$ alkyl or $C_1$–$C_6$ hydroxyalkyl, (b) a second container containing a persulfate oxidizing agent, a buffer selected from the group consisting of 2-amino-2-hydroxymethyl-1,3-propanediol and bicarbonates being present in one of said first or said second containers or in a third container, the amount of said buffer contained in the kit being sufficient to provide a pH of from 7 to 11 when the contents of the first and second containers or the first, second and third containers are mixed, and the persulfate being present in the kit an amount equal to about one to four equivalents relative to the catechol, and (c) written instructions, wherein the period of time from the mixing of the contents of the containers to form a mixture to the removal of said mixture from the hair is between about 5 to 45 minutes.

17. The kit of claim 16 further comprising a catalytic quantity of a water soluble cupric or ferrous salt contained in one of said first, second or third containers or in a fourth container.

18. The method of claim 16 or 17 wherein the catechol is a dopa species selected from the group consisting of dopa, epinephrine, cysteinyl dopa, alpha alkyl dopa having 1 to 4 carbons in the alkyl group and alkyl dopa esters having 1 to 6 carbons in the alkyl group.

19. The method of claim 18 wherein the dopa species is dopa.

20. The method of claim 16 or 17 wherein the hair dye composition additionally contains a color modifier selected from the group consisting of direct dyes, primary intermediates, couplers and mixtures thereof.

21. The kit of claim 17 wherein the amount of persulfate present in the kit is not in great excess of two equivalents relative to the catechol.

22. The kit of claim 17 or 21 wherein the salt is cupric acetate, chloride or sulfate.

* * * * *